US012290516B2

(12) United States Patent
Fu et al.

(10) Patent No.: US 12,290,516 B2
(45) Date of Patent: May 6, 2025

(54) HETEROCYCLIC COMPOUNDS AS EphA4 INHIBITORS

(71) Applicant: The Hong Kong University of Science and Technology, Hong Kong (CN)

(72) Inventors: Kit Yu Fu, Hong Kong (CN); Wing Yu Fu, Hong Kong (CN); Nancy Yuk-Yu Chu Ip, Hong Kong (CN); Shuo Gu, Zhejiang (CN); Xuhui Huang, Hong Kong (CN); Chui Fun Fanny Ip, Hong Kong (CN)

(73) Assignee: The Hong Kong University of Science and Technology, Kowloon (HK)

( * ) Notice: Subject to any disclaimer, the term of this patent is extended or adjusted under 35 U.S.C. 154(b) by 40 days.

(21) Appl. No.: 16/612,698

(22) PCT Filed: May 11, 2018

(86) PCT No.: PCT/IB2018/053315
§ 371 (c)(1),
(2) Date: Nov. 11, 2019

(87) PCT Pub. No.: WO2018/207154
PCT Pub. Date: Nov. 15, 2018

(65) Prior Publication Data
US 2020/0206220 A1    Jul. 2, 2020

Related U.S. Application Data (60) Provisional application No. 62/505,332, filed on May 12, 2017.

(51) Int. Cl.
| | | |
|---|---|---|
| *A61K 31/506* | (2006.01) |
| *A61K 9/00* | (2006.01) |
| *A61K 31/451* | (2006.01) |
| *A61K 31/46* | (2006.01) |
| *A61K 31/498* | (2006.01) |
| *A61K 31/58* | (2006.01) |
| *A61P 25/28* | (2006.01) |

(52) U.S. Cl.
CPC .......... *A61K 31/498* (2013.01); *A61K 9/0053* (2013.01); *A61K 31/451* (2013.01); *A61K 31/46* (2013.01); *A61K 31/506* (2013.01); *A61K 31/58* (2013.01); *A61P 25/28* (2018.01)

(58) Field of Classification Search
CPC ...... A61K 31/506; A61K 9/0053; A61P 25/28
See application file for complete search history.

(56) References Cited

U.S. PATENT DOCUMENTS

| 4,524,072 A | 6/1985 | Zivin |
| 4,771,056 A | 9/1988 | Rozencwaig |
| 7,687,512 B2* | 3/2010 | Bilbe .................... A61P 25/28 |
| | | 514/275 |
| 10,428,140 B2 | 10/2019 | Taguchi et al. |
| 2007/0129389 A1* | 6/2007 | Bilbe ....................... A61P 7/04 |
| | | 514/275 |
| 2008/0004286 A1 | 1/2008 | Wang et al. |
| 2012/0129834 A1 | 5/2012 | Hughes et al. |

FOREIGN PATENT DOCUMENTS

| CN | 102321142 A | 1/2012 |
| CN | 103450182 A | 12/2013 |
| CN | 105473591 B | 4/2016 |
| CN | 106163548 A | 11/2016 |
| CN | 106496193 A | 3/2017 |
| CN | 107922499 B | 8/2021 |
| CN | 106999578 B | 3/2022 |
| CN | 111320693 B | 4/2023 |
| EP | 0 214 557 A2 | 3/1987 |
| WO | WO-2009/136176 A1 | 11/2009 |
| WO | WO-2015/007222 A1 | 1/2015 |
| WO | WO-2016/019280 A1 | 2/2016 |
| WO | WO 2017/212420 | * 12/2017 |

OTHER PUBLICATIONS

Lonskaya et al., Neuroscience, 304 (2015), pp. 316-327.*
Fodor et al. (Abstract Only); Orvosi Hetilap, vol. 121, No. 27, pp. 1631-1632, 1635-9 (1980) as indexed by SciFinder.*
Pagan et al., Journal of Parkinson's Disease 6 (2016), pp. 503-517.*
Xu et al., Effect of cyproheptadine on changes of 5-HT and 5-HIAA levels in brain cortex and serum following rat brain injury, Journal of Medical Colleges of PLA, vol. 8, No. 2, pp. 179-183 (1993) [Abstract and Scifinder Cas Abstract Only].*
Bornebroek et al., Brain Pathology 6: 111-114 (1996).*
Wainberg M., et al. The effects of cyproheptadine on locomotion and on spasticity in patients with spinal cord injuries. Journal of Neurology, Neurosurgery & Psychiatry 1990;53:754-763. Abstract Only.*
International Preliminary Report on Patentability in International Application PCT/IB2018/053315 dated Nov. 21, 2019 (7 pages).
International Search Report and Written Opinion in International Application No. PCT/IB2018/053315 mailed Sep. 7, 2018 (11 pages).
Fu, et al., "Blockade of EphA4 signaling ameliorates hippocampal synaptic dysfunctions in mouse models of Alzheimer's disease", PNAS 2014, vol. 111, No. 27, pp. 9959-9964.

(Continued)

*Primary Examiner* — Alicia L Otton (74) *Attorney, Agent, or Firm* — Kilpatrick Townsend & Stockton LLP (57) ABSTRACT

New methods and kits for treating diseases caused or exacerbated by overactivated EphA4 signaling are provided. The method includes administering to a subject in need thereof an effective amount of a small molecule compound inhibitor for EphA4 signaling. Also provided are methods for identifying additional compounds as therapeutic agents useful for treating conditions involving overly active EphA4 signaling.

5 Claims, 3 Drawing Sheets

(56) References Cited

OTHER PUBLICATIONS

Goldshmit, et al., "Axonal Regeneration and Lack of Astrocytic Gliosis in EphA4-Deficient Mice", The Journal of Neuroscience 2004, 24, 10064-1007.
Spanevello, et al., "Acute Delivery of EphA4-Fc Improves Functional Recovery after Contusive Spinal Cord Injury in Rats", J. Neurotrauma 2013,30, 1023-1034.
Van Hoecke, et al., "EPHA4 is a disease modifier of amyotrophic lateral sclerosis in animal models and in humans", Nature Medicine, 2012, 18, 1418.
Vargas, et al., "Amyloid-ß oligomers synaptotoxicity: The emerging role of EphA4/c-Abl signaling in Alzheimer's disease", Biochimica et Biophysica Acta Molecular Basis of Disease 1864 (2018), 1148-1159.
Vargas, et al., "EphA4 Activation of c-Abl Mediates Synaptic Loss and LTP Blockade Caused by Amyloid-beta Oligomers", Plos One 2014, vol. 9, Issue 3.
Zhao, et al., "Decreased signalling of EphA4 improves functional performance and motor neuron survival in the SOD1G93A ALS mouse model", Scientific Reports 2018, 8, 11393.
Clinical Drug Handbook, 5th edition, Jun Huang et al., pp. 588-589, Shanghai Scientific & Technical Publishers, published on Jan. 31, 2015.
Office Action issued for CN 201880040282.4 dated Jun. 8, 2022.
Collection of Clinical Applications of Drugs, Genshan NI, p. 782, PLA News Media Center press, 1994.
David et al., 2009 Neuron 62, 479-93.
Fang et al. 2013 Neuron 79, 665-79.
Faruqi, Nat Rev Drug Discov. 11(10):747, 2012.
Hauser and Oksenberg 2006 Neuron 52(1):61-76.
Hernandez-Pedro et al. 2013 Clin Dev Immunol. 413-465.
Lee et al., 2013 Curr Top Behav Neurosci 14, 153-79.
Lemmens et al., Hum Mol Genet. 22(11):2214-20, 2013.
Li et al., Neurosci Lett. 518(2):92-5, 2012.
Masi and Brovedani, 2011 CNS Drugs 25, 913-31.
Munoz et al. 2002 J Immunol. 169(1): 177-845.
Parmentier-Batteur et al. 2011 J Neurochem. 118(6):1016-31.
Sobel 2005 Brain Pathol. 15(1):35-45.

* cited by examiner

HETEROCYCLIC COMPOUNDS AS EphA4 INHIBITORS

CROSS REFERENCE TO RELATED APPLICATION

This application is a US national phase application under 35 USC § 371 of International Application No. PCT/IB2018/053315, filed on May 11, 2018, which claims the benefit of priority to U.S. Provisional Application 62/505,332, filed May 12, 2017, the contents of each of which are incorporated by reference in their entireties.

BACKGROUND

Alzheimer's disease (AD) is the most common form of dementia and involves accumulation of amyloid plaques and neurofibrillary tangles in brains. The receptor tyrosine kinase erythropoietin-producing hepatocellular A4 (EphA4) was recently found to be a new target for the treatment of AD.

Erythropoietin-producing hepatocellular (Eph) receptors, the largest family of receptor tyrosine kinases, are involved in a diverse spectrum of cellular processes[1]. Eph receptors are activated by binding with their transmembrane ligands, ephrins, to generate bidirectional signals via cell-cell interactions. The Eph receptors are subdivided into EphA (EphA1-EphA8 and EphA10) and EphB (EphB1-EphB4 and EphB6). EphA receptors preferentially bind to their cognate ligands, ephrin-As (ephrin-A1-ephrin-A5), which are anchored to the membrane via glycosylphosphatidylinositol linkage; while EphB receptors preferentially bind to ephrin-Bs (ephrinB1-ephrinB3), which are transmembrane proteins.

Among the Eph receptors, EphA4 is unique because it can interact with most ephrin-As and ephrin-Bs. Furthermore, EphA4 plays an essential role in different developmental processes and functioning, in particular, neuronal migration and neural circuit formation during brain development as well as synapse development and synaptic plasticity. The deregulated expression or aberrant increased activity of EphA4 is a feature of various human diseases such as Alzheimer's disease (AD) and cancers including breast cancer and pancreatic cancer.

SUMMARY

In one aspect, the present technology provides a method for treating a disease or condition that is caused or exacerbated by EphA4 signaling, especially in the case of excessively activated EphA4 signaling. Neurodegenerative disorders known to involve over-activated EphA4 signaling include, for example, amyloid β-induced neurological disorders such as Alzheimer's Disease, spinal cord injury, Parkinson's Disease, head injury (e.g., traumatic brain injury), peripheral nerve regeneration, amyotrophic lateral sclerosis (ALS, often referred to as Lou Gehrig's Disease), stroke, hearing disorders, multiple sclerosis, mood disorders, various types of cancers. The methods include administering to the subject an effective amount of a small molecule inhibitor for EphA4 signaling as described herein.

In some embodiments of the method of treating a disease involving EphA4 signaling, the compound is selected from among those described in Table 1. In some embodiments, the compound is selected from ergoloid, cyproheptadine, nilotinib, abiraterone, and retapamulin, as well as other small molecule compounds.

These EphA4 inhibitors are useful for the purpose of treating a disease or condition involving over-active EphA4 signaling, include Alzheimer's disease and others diseases caused by amyloid β-induced neurotoxicity. For the purpose of practicing the present technology, however, any one or any combination of the previously known EphA4 inhibitors may be excluded from the practice scope in some embodiments.

In addition, this technology also provides pharmaceutical compositions useful for the purpose of treating diseases or conditions involving overactive EphA4 signaling, especially those involving plaque or aggregate formation (e.g., amyloid β-related neurodegenerative disorders such as Alzheimer's disease), including but not limited to the diseases and conditions named above. In additional to Alzheimer's disease, the pharmaceutical compositions comprising the EphA4 signaling inhibitors (including the small molecule compounds disclosed herein) may be used to treat diseases and disorders such as amyotrophic lateral sclerosis (ALS), stroke, cancer, and spinal cord injury, all of which have a component of over-active or excessive cellular signaling mediated by EphA4. An amyloid β-related neurodegenerative disorder is a degenerative neurological disorder in which the presence of amyloid plaques contributes to the onset and/or progression of the disorder. One example of such disorders is Alzheimer's Disease. In some embodiments of this technology, motor neuron disorders as conventionally defined are excluded from the class of "amyloid β-related neurodegenerative disorders."

In another aspect, provided are compositions designed for the treatment, management, or prevention of a disease or condition involving over-active EphA4 signaling. The composition typically comprises an inhibitor for EphA4 signaling as the active ingredient and a pharmaceutically or physiologically acceptable excipient. The EphA4 inhibitors may be formulated for various modes of delivery, e.g., for oral administration or injection, to a patient in need of such treatment.

In some embodiments, the compositions comprise an EphA4 inhibitor that is a small molecule compound, for example, including any of those disclosed herein including in Table 1. The EphA4 inhibitors described herein therefore may be used for the manufacture of medicament intended for treating diseases and conditions involving over-active EphA4 signaling, including but not limited to Alzheimer's disease, ALS, Parkinson's Disease, traumatic brain injury, stroke, cancer, and spinal cord injury.

In yet another aspect, the present technology provides a method for identifying compounds that can be used as therapeutic agents for treating neurodegenerative diseases (especially an amyloid β-related neurodegenerative disorder such as Alzheimer's Disease) by way of identifying new, previously unknown inhibitors of EphA4 signaling. In some cases, a candidate compound is tested for its ability to interfere with and therefore reduce the binding between EphA4 and its ligand (e.g., an ephrin). Potentially, an inhibitor may be a molecule of any chemical nature, including small molecules, macromolecules (such as polypeptide and polynucleotides), and the like. Typically, the candidate compound being tested for its ability to interrupt EphA4-ligand binding is first placed in an environment where both EphA4 and its ligand are present and under the conditions that are permissible for the specific binding between EphA4 and its ligand. The level of binding between EphA4 and the ligand with the candidate compound present is then determined and compared with the level of binding between EphA4 and its ligand under the same conditions except that the candidate compound is absent (in other words, a "control binding level" of EphA4 and the ligand). If the EphA4-ligand binding level is lower than the control binding level, for example, by at least 10%, 20%, 30%, 40%, 50%, 60%, 70%, 75%, 80%, 85%, 90%, 95% or even higher, the binding between EphA4 and its ligand is deemed "inhibited" and the candidate compound is deemed an EphA4 signaling inhibitor, at least preliminarily. Optionally, an additional step of further testing is carried out to verify the compound's function to provide neuroprotection by suppressing EphA4 signaling. For example, an animal model such as the AD mouse model APP/PS1 described in this application may be used to verify whether a compound capable of interrupt EphA4-ligand binding has an effect on improving hippocampal synaptic plasticity inhibited by amyloid plaques, as well as on improving certain features of the AD pathology, e.g., reduced amyloid plaques in the cortex and hippocampus.

As described in this disclosure, for the purpose of screening for small molecule EphA4 inhibitors, one often first performs a molecular docking analysis using a small molecule library. The small molecules that are predicted to bind with EphA4 are selected. In the alternative, small molecules may be first screened and selected for their ability to specifically bind EphA4 in a cell-based or cell-free binding assay format, often in competition against a native ligand for EphA4 such as an ephrin. These selected small molecules are then tested for their ability in inhibiting EphA4 in cellular and animal models. The candidate small molecules (typically at 1 μM to 10 μM) are tested for their ability in inhibiting the EphA4-dependent growth cone collapse using cultured hippocampal neurons. When the small molecules show inhibition on the EphA4-dependent growth cone collapse assay at a dosage-dependent manner, the ability of these small molecules on blocking the ephrin-A dependent autophosphorylation of EphA4 (which reflects the activation status of the receptor) in cultured cortical neurons are examined using Western blot analysis. After it is demonstrate that these small molecules are EphA4 inhibitors in cellular assays, further testing is then performed to determine whether these small molecules are able to reverse the amyloid β-induced reduction of long-term potentiation (LTP; a form of synaptic plasticity) in acute hippocampal organotypic slices. When the results are positive, oral administration of AD mouse models (e.g., APP/PS1 and APP mutant mouse models) with these small molecules are performed. Whether the small molecules can reverse the inhibition of LTP and reduce the pathological hallmarks (amyloid β deposition, astrogliosis and microgliosis) in these AD mouse models is assessed. In addition, biochemical analysis is performed to show that the small molecules bind directly to the extracellular domain of EphA4, but not the other members of the Eph family. The same or similar screening process can be followed for the purpose of identifying EhpA4 inhibitors of any chemical nature.

Another type of EphA4 signaling inhibitor acts by suppressing the expression of EphA4 or its ligand, and such suppression may be at RNA level and/or protein level. Many molecules can fall into this category, for example anti-sense oligonucleotides, microRNAs, or antibodies that specifically target EphA4 transcript (or the transcript of an EphA4 ligand) for hastened degradation can be effective inhibitors of EphA4 signaling. A proposed inhibitor of this nature may be tested by exposing to a cell that expresses EphA4 (or its ligand) for any reduction in EphA4 (or its ligand). Again, such reduction is a reduction of at least 10%, 20%, 30%, 40%, 50%, 60%, 70%, 75%, 80%, 85%, 90%, 95% or even higher, when compared to the expression level of EphA4 (or its ligand) under the same conditions but in the absence of the proposed inhibitor. Once a reduction in EphA4 (or its ligand) expression is detected, the proposed inhibitor may be further tested in the same fashion described above to verify its neuroprotective activity.

In one aspect, the present technology provides a kit for use in the treatment of a disease or disorder caused or exacerbated by EphA4 signaling, e.g., an amyloid β-induced neurotoxicity such as Alzheimer's Disease. The kit contains one or more inhibitors of EphA4 signaling, such as by way of disrupting EphA4-ligand binding or by way of suppressing EphA4 or ligand expression (e.g., at the RNA level or at the protein level). In some embodiments, the kit comprises an EphA4 inhibitor that is a small molecule compound as disclosed herein, including one or more of those disclosed in Table 1. The kit often includes multiple containers, each of which contains the EphA4 signaling inhibitor in a daily administration dosage, such that the kit can provide the inhibitor for daily use by a patient during a certain time period. In some cases, the inhibitor is formulated in a pharmaceutical composition suitable for oral administration, or for injection such as intravenous injection, subcutaneous injection, or intramuscular injection. Optionally, an instruction manual directing the user on the administration of the inhibitor is also provided in the kit.

BRIEF DESCRIPTION OF DRAWINGS

FIG. 2. Molecular docking analysis. (a) Cavity of the EphA4 ligand binding domain; and docking conformations of small molecule compounds (b) ergoloid, (c) cyproheptadine, (d) nilotinib, (e) abiraterone, and (f) retapamulin in complex with EphA4. The conformations of lowest docking energy were selected for analysis. The proteins are shown in surface representation (b-f), whereas drugs are shown as sticks.

DETAILED DESCRIPTION

The examples of this application are provided by way of illustration only and not by way of limitation. Those of skill in the art will readily recognize a variety of non-critical parameters that could be changed or modified to yield essentially the same or similar results.

The terms "a," "an," or "the" as used herein not only include aspects with one member, but also include aspects with more than one member. For example, an embodiment of a method of treatment that comprises using a compound set forth in claim 1 would include an aspect in which the method comprises using two or more compounds set forth in claim 1.

The term "about" as used herein to modify a numerical value indicates a defined range around that value. If "X" were the value, "about X" would indicate a value from 0.9X to 1.1X, and in some embodiments, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

When the quantity "X" only allows whole-integer values (e.g., "X carbons") and X is at most 15, "about X" indicates from (X−1) to (X+1). In this case, "about X" as used herein specifically indicates at least the values X, X−1, and X+1. If X is at least 16, the values of 0.90X and 1.10X are rounded to the nearest whole-integer values to define the boundaries of the range.

When the modifier "about" is applied to describe the beginning of a numerical range, it applies to both ends of the range. Thus, "from about 50 to 250 mg" is equivalent to "from about 50 to about 250 mg." When "about" is applied to describe the first value of a set of values, it applies to all values in that set. Thus, "about 100, 150, or 200 mg," is equivalent to "about 100 mg, about 150 mg, or about 200 mg." However, when the modifier "about" is applied to describe only the end of the range or only a later value in the set of values, it applies only to that value or that end of the range. Thus, the range "about 5 to 9" is the same as "about 5 to about 9," but the range "5 to about 9" is not.

In general, the unit prefix "u" as used herein is equivalent to "μ" or "micro." For example, "ul" is equivalent to "μl" or "microliters."

The present technology provides methods to identify small molecules that target the LBD of EphA4, e.g., inhibitors of EphA4 signalling. An exemplary list of such compounds along with their structure and docking energy is presented in Table 1.

Compounds described in this application are useful for treating a variety of diseases and conditions including neurodegenerative disorders involving over-activated EphA4 signaling, for example, amyloid β-induced neurological disorders such as Alzheimer's Disease, spinal cord injury, Parkinson's Disease, head injury (e.g., traumatic brain injury), peripheral nerve regeneration, amyotrophic lateral sclerosis (ALS), stroke, hearing disorders, multiple sclerosis, mood disorders, and cancers. In particular, they are useful, when administrated in an effective amount to a patient in need thereof, for the treatment of stroke, ALS, spinal cord injury, and cancers. The term "effective amount," as used herein, refers to an amount that produces therapeutic effects for which a substance is administered. The effects include the prevention, correction, or inhibition of progression of the symptoms of a disease/condition and related complications to any detectable extent. The exact amount will depend on the nature of the therapeutic agent, the manner of administration, and the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The EphA4 receptor is indicated as a therapeutic target for a number of ailments. For example, the EphA4 signal pathway is linked to the apoptotic cell death resulting from ischemia. The expression of ephrinA3 and EphA4 is significantly increased in the hippocampus following transient forebrain ischemia. Inhibition of EphA4, however, reduces apoptotic neuronal cell death, thus indicating that EphA4 signalling is involved in apoptosis after ischemia (Li et al., *Neurosci Lett.* 518(2):92-5, 2012). Furthermore, a recent study shows that pharmacological inhibition of the EphA4 signaling cascade affects functional recovery, and more specifically, improves motor function after ischemic stroke (Lemmens et al., *Hum Mol Genet.* 22(11):2214-20, 2013).

EphA4 inhibition also rescues neurodegeneration in amyotrophic lateral sclerosis (ALS), a fatal neurodegenerative disease characterized by the progressive degeneration of motor neurons. It has been shown that motor neurons that are most susceptible to degeneration in ALS express higher levels of EphA4. Furthermore, an inverse correlation between EPHA4 expression and disease onset and survival, has been observed in ALS patients. Moreover, EphA4 knockdown rescues axonopathy induced by expression of mutant TAR DNA-binding protein 43, another protein that causes familial ALS. These findings indicate that EphA4 modulates motor neuron degeneration and disease progression in ALS, and highlights the use of EphA4 inhibition as a therapeutic strategy in ALS (Faruqi, *Nat Rev Drug Discov.* 11(10):747, 2012; Van Hoecke et al., *Nat Med.* 18(9):1418-22, 2012).

EphA4 inhibition also shows promising therapeutic potential in spinal cord injury (SCI). Individuals with SCI are often paralyzed with little chance of regaining loss of function due to limited ability of axons to grow and regenerate. However, EphA4 has recently been implicated in axonal inhibition and astrocytic gliosis. Mice lacking the EphA4 gene exhibit less gliosis and significantly reduced glial scars in their lesioned cords after spinal cord hemisection, and further, neurological outcome in EphA4$^{-/-}$ mice is dramatically improved compared to wild-type controls (Goldshmit et al., *J Neurosci.* 24(45):10064-73, 2004). Furthermore, administration of an EphA4 inhibitor has demonstrated significant recovery in locomotor function after SCI in an animal model of SCI (Spanevello et al., *J Neurotrauma.* 30(12):1023-34, 2013).

EphA4 is also implicated in cancer. The receptor is upregulated in various human cancers such as gastric cancer (Oki et al., *World J Gastroenterol.* 14:5650-5656, 2008; Miyazaki et al., *BMC Clin Pathol.* 13:19, 2013), colorectal cancer (Oshima et al., *Int J Oncol.* 33:573-577, 2008), and pancreatic cancer (Liu et al., *Oncol Lett.* 7(6):2165-2169, 2014). High expression of EphA4 is correlated with tumor progression, including the invasion, pathological stage and distant metastasis (Miyazaki et al., *BMC Clin Pathol.* 13:19, 2013). For example, EphA4 expression in brain tumors has been shown to be 4-fold higher than in normal brain tissue. Furthermore, EphA4 also plays an important role in malignant phenotypes of glioblastoma by promoting the proliferation and migration of glioma cells (Fukai et al., *Mol Cancer Ther.* 7(9):2768-78, 2008). Thus, EphA4 inhibitors are important therapeutic agents in anticancer treatment strategies.

Furthermore, EphA4 plays a role in adult neurogenesis, which is a process of producing functional neurons from proliferating cells called neural progenitor cells in the adult brain. Both in vivo and in vitro studies suggest that this process can be modulated by various environmental factors. For instance, enriched environment, exercise and learning, can stimulate adult neurogenesis while chronic stress or aging affect in the opposite way. Accumulating evidence further suggests that the etiology of depression is highly related to defective adult neurogenesis in hippocampus (Masi and Brovedani, 2011 *CNS Drugs* 25, 913-31; Lee et al., 2013 *Curr Top Behav Neurosci* 14, 153-79). Chronic stress causes suppression of adult neurogenesis, probably due to the elevated level of glucocorticoid release. Additionally, antidepressant treatment (e.g., imipramine and fluoxetine) are shown to upregulate neurogenesis in the adult brain, which further support the notion that adult neurogenesis is a core factor in the pathology of depression (Lee et al., 2013 *Curr Top Behav Neurosci* 14, 153-79; Fang et al. 2013

Neuron 79, 665-79; David et al., 2009 Neuron 62, 479-93). Agents that can stimulate adult neurogenesis provide a new therapeutic strategy for treating depression. The small molecule compounds that have EphA4 inhibitor activity described herein are therefore also useful for treating neurological/psychiatric disorders such as anxiety and depression.

Multiple sclerosis (MS) is another disease that may be treated by the EphA4 inhibitors described herein. MS is the most common disabling neurologic disease of young adults (Hauser and Oksenberg 2006 Neuron 52(1):61-76). It is an autoimmune disease of the central nervous system with widespread focal lesions of primary demyelination leading to variable axonal, neuronal and astroglia injury (Lassmann 2013 Exp Neurol. S0014-4886(13)00361-0). Demyelination, the hallmark of MS, disrupts neuronal communication resulting in a wide range of symptoms (Hernández-Pedro et al. 2013 Clin Dev Immunol. 413-465). The initial inflammatory cascade is thought to originate from the activation of resident cells in the CNS, leading to tissue destruction, demyelination, and progressive neurological dysfunction (Hernández-Pedro et al. 2013 Clin Dev Immunol. 413-465). Ephrins and Ephs not only play important roles such as synaptic plasticity and neural stem cell function, they are also involved in immunologic functions such as in thymic development and T/B-cell signaling (Sobel 2005 Brain Pathol. 15(1):35-45; Muñoz et al. 2002 J Immunol. 169(1): 177-845). Blockade of EphA4 inhibited wound closure and reduced the accumulation of reactive astrocytes in the scratch wound model (Parmentier-Batteur et al. 2011 J Neurochem. 118(6):1016-31). Aberrant ephrin/Eph expression is involved in the immunopathogenesis of lesions and in neuronal injury in multiple sclerosis (MS) (Sobel 2005 Brain Pathol. 15(1):35-45). In another study in human MS patients, an increase in EphA4 protein was found in active MS lesions relative to those in chronic MS lesions (Parmentier-Batteur et al. 2011 J Neurochem. 118(6):1016-31). Taken together, these studies support a role for the activation of EphA4 in the development of the damage after acute CNS injury, including MS, and that inhibition of EphA4 (e.g., via the action of a EphA4 inhibitor, such as the small molecule compounds described herein) is a therapeutic strategy that promotes CNS functional recovery in MS and other neurodegenerative diseases.

A pharmaceutical composition made for the use of treating diseases or conditions involving over-active EphA4 signaling typically comprises one EphA4 inhibitor (e.g., any one of the inhibitors identified herein) as the active ingredient and a pharmaceutically/physiologically acceptable excipient or carrier. Such composition may be specifically formulated for the intended route of administration to the patients, for example, via oral administration or injection. The EphA4 inhibitors are also useful for the purpose of manufacturing medicament for the treatment of relevant diseases as described in this application.

The present technology also provides pharmaceutical compositions or physiological compositions comprising an effective amount of a compound that inhibits EphA4-mediated signaling and therefore provide the intended benefits in both prophylactic and therapeutic applications. Such pharmaceutical or physiological compositions also include one or more pharmaceutically or physiologically acceptable excipients or carriers. Pharmaceutical compositions of the present technology are suitable for use in a variety of drug delivery systems. Suitable formulations for use in the present technology are found in Remington's Pharmaceutical Sciences, Mack Publishing Company, Philadelphia, Pa., 17th ed. (1985). For a brief review of methods for drug delivery, see, Langer, Science 249: 1527-1533 (1990).

The pharmaceutical compositions of the present technology can be administered by various routes, e.g., oral, subcutaneous, transdermal, intramuscular, intravenous, or intraperitoneal. In some embodiments, the routes of administering the pharmaceutical compositions are local delivery to an organ or tissue suffering from a condition exacerbated by EphA4-mediated signaling in a human at daily doses of about 0.01-2500 mg, or even 2.5-500 mg per day. The appropriate dose may be administered in a single daily dose or as divided doses presented at appropriate intervals, for example as two, three, four, or more subdoses per day.

For preparing pharmaceutical compositions containing an EphA4 inhibitor such as those shown in Table 1, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., an EphA4 inhibitor in Table 1. In tablets, the active ingredient (an inhibitor of EphA4 signaling) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets may contain between about 5% to about 70% by weight of the active ingredient of an inhibitor of EphA4-mediated signaling. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of an EphA4 inhibitor with encapsulating material as a carrier providing a capsule in which the inhibitor (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., an EphA4 inhibitor such as one found in Table 1) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., an EphA4 signaling inhibitor) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, or from 5 to 9, or even from 7 to 8.

The pharmaceutical compositions containing an EphA4 inhibitor can be administered for prophylactic and/or therapeutic treatments. In therapeutic applications, compositions are administered to a patient already suffering from a condition that may be exacerbated by the EphA4-mediated cellular signaling in an amount sufficient to prevent, cure, reverse, or at least partially slow or arrest the symptoms of the condition and its complications, such as the onset, progression, and metastasis of certain types of cancer. An amount adequate to accomplish this is defined as a "therapeutically effective dose." Amounts effective for this use will depend on the severity of the disease or condition and the weight and general state of the patient, but generally range from about 0.1 mg to about 2,500 mg of the inhibitor per day for a 70 kg patient, with dosages of from about 2.5 mg to about 500 mg of the inhibitor per day for a 70 kg patient being more commonly used.

In prophylactic applications, pharmaceutical compositions containing an EphA4 inhibitor are administered to a patient susceptible to or otherwise at risk of developing a disease or condition in which excessive EphA4-mediated signaling is undesirable, in an amount sufficient to delay or prevent the onset of the symptoms. Such an amount is defined to be a "prophylactically effective dose." In this use, the precise amounts of the inhibitor again depend on the patient's state of health and weight, but generally range from about 0.1 mg to about 2,500 mg of the inhibitor for a 70 kg patient per day, more commonly from about 2.5 mg to about 500 mg for a 70 kg patient per day.

Single or multiple administrations of the compositions can be carried out with dose levels and pattern being selected by the treating physician. In any event, the pharmaceutical formulations should provide a quantity of an EphA4 inhibitor sufficient to effectively inhibit cellular signaling mediated by EphA4 in the patient, either therapeutically or prophylatically.

Kits

The present technology also provides kits for inhibiting EphA4 signaling and therefore for treating AD according to the method of the present technology. The kits typically include a container that contains (1) a pharmaceutical composition having an effective amount of an inhibitor of EphA4-mediated signaling (for instance, a compound identified in Table 1) and (2) informational material containing instructions on how to dispense the pharmaceutical composition, including description of the type of patients who may be treated (e.g., patients suffering from Alzheimer's Disease, ALS, stroke, or various types of cancer with excessive EphA4 signaling), the schedule (e.g., dose and frequency) and route of administration, and the like.

EXAMPLES

Example 1: Identification of Small Molecule EphA4 Inhibitor Identified by Virtual Screening (A) Virtual Screening of DrugBank Small Molecule Database by Molecular Docking Detailed structural analysis of EphA4-ligand complex provides a promising basis for the virtual screening of small molecules that modulate EphA4-ligand interaction. In particular, the uniqueness of the ligand-binding pocket in the ectodomain of EphA4 renders the receptor an ideal target for small molecule screening. Virtual screening of EphA4 inhibitor candidates through molecular docking was performed using AutoDock Vina to estimate the binding energy of the ligand and target. AutoDock 4.0 was employed to perform the docking between EphA4 (PDB code 2WO2) and FDA-approved small molecule drugs in DrugBank containing 1317 chemical compounds. AutoDock Tools was used to prepare the protein by merging nonpolar hydrogens and to add Gasteiger partial charges. Each drug with the assignments of partial charge and bond type was prepared. The docking grid box was centered between the J-K loop and D-E loop, with a volume of 22×20×22 Å. Finally, each docking simulation had 48 (parameter: exhaustive) parallel runs.

Molecular docking was performed between the extracellular domain of EphA4 and EphA4 inhibitor database containing 1317 compounds together with rhy, an EphA4 inhibitor, previously identified by high-throughput screening. In the docking analysis, Rhy had a docking energy of −9.0 kcal/mol. Accordingly, the threshold docking energy value was set to 10.0 kcal/mol in order to identify more potent candidates for experimental validation. Out of the over 1300 compounds tested, 43 compounds with a docking energy≤−10.0 kcal/mol were selected for further testing. These drugs are listed in Table 1. The candidate compounds usually have an elongated scaffold and several rings, indicating that they are compatible with the shape and hydrophobic nature of the binding site.

(B) Experimental Validation

Figure 1:
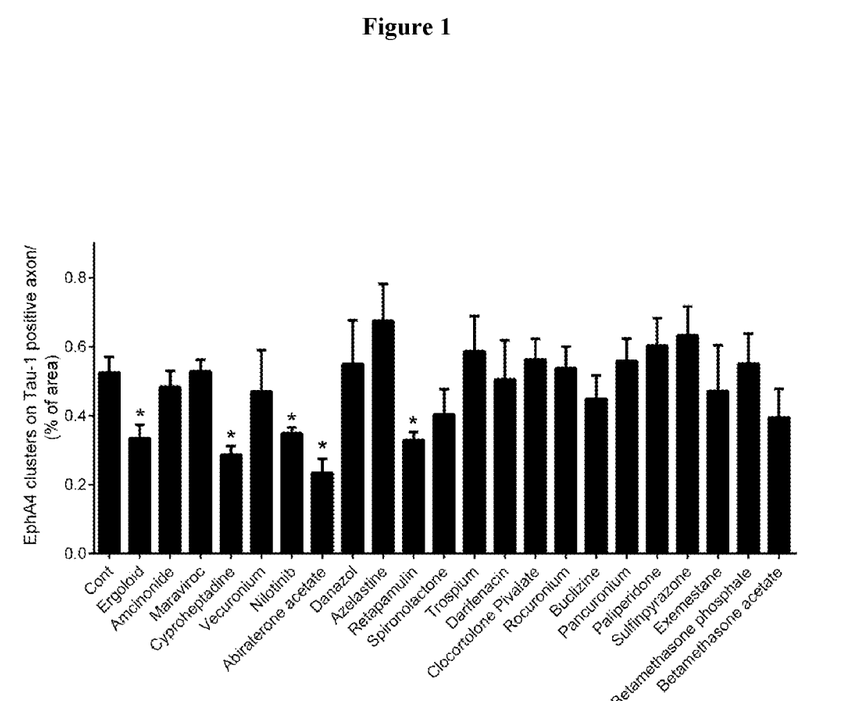
FIG. 1. Inhibitory effect of small molecule compounds on EphA4 signaling. Inhibitory activity of 22 selected FDA-approved drugs in ephrin-A1-induced EphA4 clusters in cultured hippocampal neurons. n=4 neuronal cell cultures; *p<0.05 vs. Cont; unpaired Student's t-test.

The inhibitory activity of the 22 drugs listed in Table 1 was examined using an ephrin-A1-induced EphA4 clustering assay in cultured hippocampal neurons. As shown in FIG. 1, it was found that five drugs, namely, ergoloid, cyproheptadine, nilotinib, abiraterone, and retapamulin, inhibited the ephrin-A1-induced EphA4 clustering (30% at a dose of 50 µM).

The whole extracellular domain of EphA4 is crystallized in its dimer or trimer form with or without ephrins. This domain is composed of J-K and D-E loops that form complexes with its cognate ephrin ligands in a sandwich manner. While the D-E loop is always a beta-hairpin, the J-K loop can adopt various conformations in different environments. To date, there are three crystal structures of human EphA4 LBD available in the Protein Data Bank (PDB): one in apo form (PDB ID: 2WO1) and the other two in holo forms (PDB IDs: 2WO2 and 2WO3). These three structures of EphA4 LBD are very similar, except for the J-K loop. The interaction of LBD with ephrin naturally induces different conformations of the J-K loop, which is quite different from that in the apo form. Specifically, the J-K loop in 2WO1 is a beta-hairpin, while the corresponding part in 2WO2 is a loop conformation with ephrin-B2 and that in 2WO3 is an alpha-helix secondary structure with ephrin-A2. Furthermore, the distance between the J-K and D-E loops also varies, rendering different sizes of the cavity.

Figure 2:
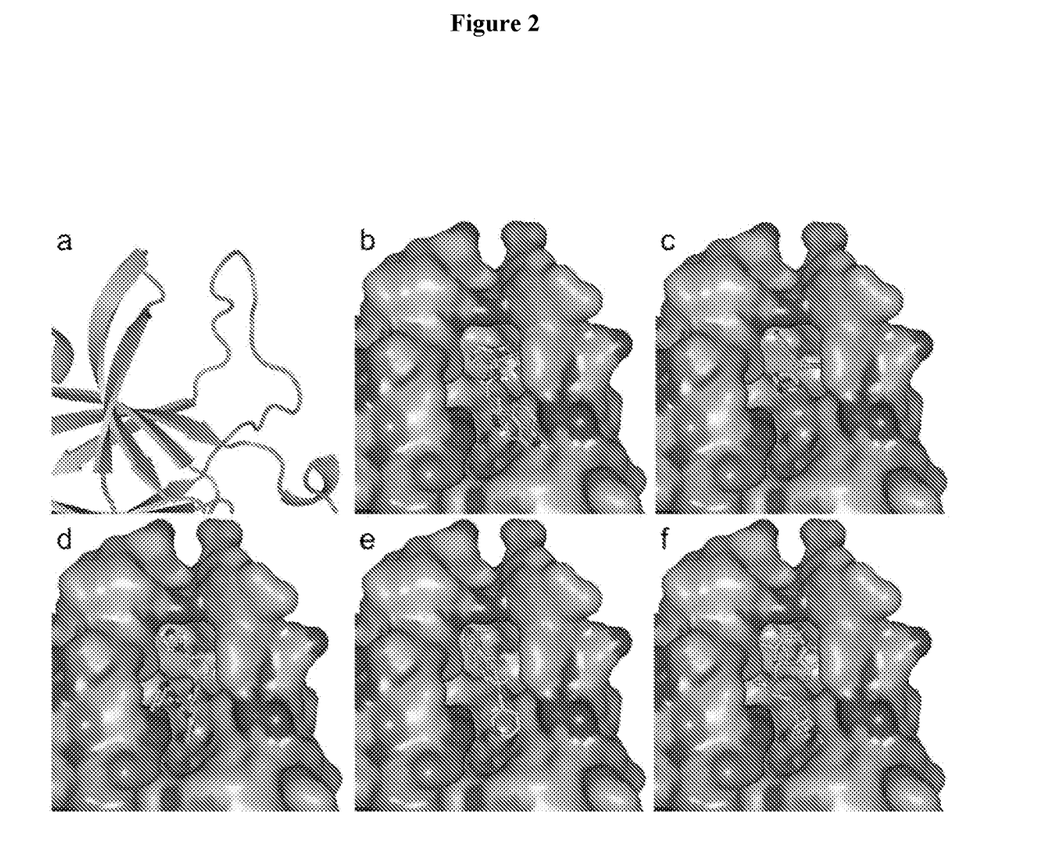

The interactions of the EphA4 ligand binding domain with the five experimentally validated drugs are depicted in FIG. 2. Despite a few hydrogen bonds, binding was mainly achieved through hydrophobic interactions via several essential residues in the cavity: F154, V157, and L166 in the J-K loop as well as 159 in the D-E loop.

Example 2: Eroloid, is an Inhibitor of EphA4

Ergoloid is used to relieve the signs and symptoms of decreased mental capacity due to the aging process. It is also used to treat some mood or behavior disorders, or other problems that may be due to changes in the brains of patients with AD or multiple small strokes. The binding of ergoloid to EphA4 is established by the hydrogen bond with D158 in the J-K loop and hydrophobic interactions with 159, F154, V157, and V195.

Example 3: Cyproheptadine is an Inhibitor of EphA4

Cyproheptadine is an H1-receptor antagonist and serotonergic antagonist. Because of its hydrophobic nature, cyproheptadine binds EphA4 via pure hydrophobic interactions with 159, F154, V157, M164, L166, A193, and V195.

Example 4: Nilotinib is an Inhibitor of EphA4

Figure 3:
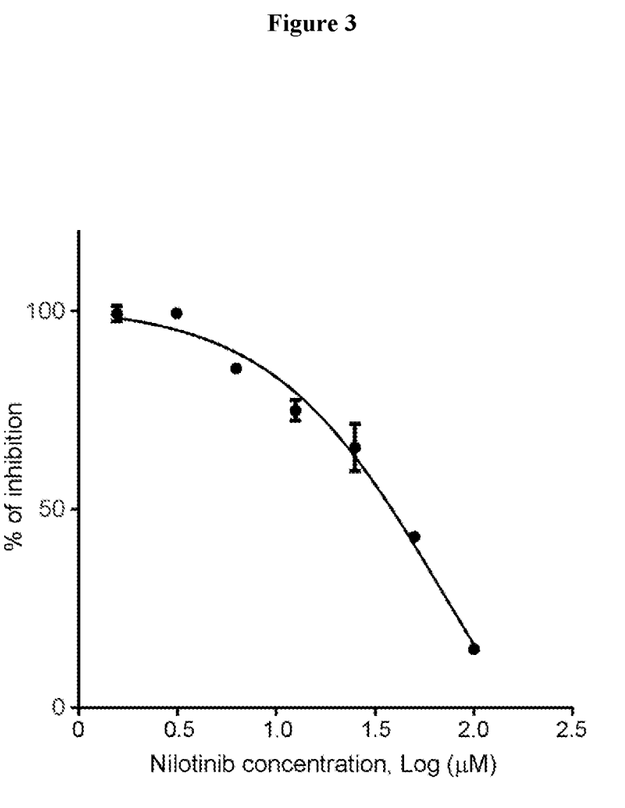
FIG. 3. Nilotinib exhibits EphA4 inhibition activity. Dose-response curve of nilotinib against the interaction of mouse EphA4 with ephrin-A1.

Nilotinib is a kinase inhibitor that targets the following kinases: BCR-ABL, KIT, LCK, EPHA3, EPHA8, DDR1, DDR2, PDGFRB, MAPK11, and ZAK. Nilotinib is predicted to form hydrogen bonds with Q70 in the D-E loop and T104. It also has hydrophobic interactions with F154, V157, 1163, L166, A193, and V195. As shown in FIG. 3, nilotinib inhibited the interaction between the extracellular domain of mouse EphA4 and ephrin-A1 in a dose-response ELISA assay and the $IC_{50}$ was measured to be 70.67 μM.

Example 5: Abiraterone is an Inhibitor of EphA4

Abiraterone acetate is combined with prednisone to treat patients with metastatic castration-resistant prostate cancer before chemotherapy. The binding of abiraterone to EphA4 is achieved by a hydrogen bond with E62 in the D-E loop as well as hydrophobic interactions with 159, F154, V157, M164, L166, A193, and V195.

Example 6: Retapamulin is an Inhibitor of EphA4

Retapamulin is used for the treatment of bacterial skin infections such as impetigo. As an antibacterial agent, specifically a protein synthesis inhibitor, retapamulin selectively inhibits bacterial protein synthesis by interacting at a site on the 50S subunit of the bacterial ribosome via an interaction that differs from those of other antibiotics. Retapamulin forms a hydrogen bond with T104 and has hydrophobic interactions with 159, F154, V157, L166, 193A, and V195.

All patents, patent applications, and other publications, including GenBank Accession Numbers, cited in this application are incorporated by reference in the entirety for all purposes.

TABLE 1

| Compound | Structure | Docking Energy (kcal/mol) |
|---|---|---|
| Dutasteride |  | −11.6 |
| Irinotecan |  | −11.3 |

TABLE 1-continued

| Compound | Structure | Docking Energy (kcal/mol) |
|---|---|---|
| Ergoloid |  | −11.1 |
| Tolvaptan |  | −11.0 |
| Conivaptan |  | −10.8 |
| Dihydroergotamine |  | −10.7 |

TABLE 1-continued

| Compound | Structure | Docking Energy (kcal/mol) |
|---|---|---|
| Pimozide |  | −10.7 |
| Adapalene |  | −10.7 |
| Amcinonide |  | −10.6 |
| Maraviroc |  | −10.6 |

TABLE 1-continued

| Compound | Structure | Docking Energy (kcal/mol) |
|---|---|---|
| Cyproheptadine |  | −10.5 |
| Vecuronium |  | −10.5 |
| Drispirenone |  | −10.5 |
| Nilotinib |  | −10.4 |
| Hexafluorenium |  | −10.4 |

TABLE 1-continued

| Compound | Structure | Docking Energy (kcal/mol) |
|---|---|---|
| Glyburide | | −10.4 |
| Abiraterone acetate | | −10.4 |
| Danazol | | −10.4 |
| Azelastine | | −10.4 |
| Ergotamine | | −10.4 |

TABLE 1-continued

| Compound | Structure | Docking Energy (kcal/mol) |
|---|---|---|
| Eplerenone |  | −10.4 |
| Retapamulin |  | −10.4 |
| Spironolactone |  | −10.3 |
| Trospium |  | −10.3 |
| Darifenacin |  | −10.2 |

TABLE 1-continued

| Compound | Structure | Docking Energy (kcal/mol) |
| --- | --- | --- |
| Clocortolone pivalate | | −10.2 |
| Irbesartan | | −10.2 |
| Deferasirox | | −10.2 |
| Rocuronium | | −10.1 |
| Betamethasone phosphate | | −10.1 |

TABLE 1-continued

| Compound | Structure | Docking Energy (kcal/mol) |
|---|---|---|
| Buclizine |  | −10.1 |
| Betamethasone acetate |  | −10.1 |
| Flucinonide |  | −10.1 |
| Pancuronium |  | −10.1 |
| Difenoxin |  | −10.1 |

TABLE 1-continued

| Compound | Structure | Docking Energy (kcal/mol) |
| --- | --- | --- |
| Paliperidone | | −10.1 |
| Diflorasone diacetate | | −10.0 |
| Lurasidone | | −10.0 |
| Vilazodone | | −10.0 |
| Telaprevir | | −10.0 |

TABLE 1-continued

| Compound | Structure | Docking Energy (kcal/mol) |
|---|---|---|
| Sulfinpyrazone | | −10.0 |
| Dexamethasone acetate | | −10.0 |
| Exemestane | | −10.0 |

What is claimed is:

1. A method for treating a subject suffering from a spinal cord injury, comprising administering to the subject an effective amount of nilotinib.

2. The method of claim 1, wherein the nilotinib is present in a pharmaceutical composition along with a pharmaceutically acceptable excipient.

3. The method of claim 2, comprising daily administration of nilotinib to the subject.

4. The method of claim 2, wherein the nilotinib is present in a daily administration dosage in the pharmaceutical composition.

5. The method of claim 2, wherein the pharmaceutical composition is formulated for oral administration.

* * * * *